(12) United States Patent
Ilter et al.

(10) Patent No.: US 9,259,297 B2
(45) Date of Patent: Feb. 16, 2016

(54) DENTAL IMPLANT AND ABUTMENT SYSTEM

(75) Inventors: Emily Ilter, San Diego, CA (US); Ayra A. Baker, Escondido, CA (US); Erika Echeverria, Encinitas, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 0 days.

(21) Appl. No.: 13/825,596

(22) PCT Filed: Jul. 13, 2011

(86) PCT No.: PCT/US2011/043784
§ 371 (c)(1),
(2), (4) Date: Sep. 10, 2013

(87) PCT Pub. No.: WO2012/039819
PCT Pub. Date: Mar. 29, 2012

(65) Prior Publication Data
US 2014/0147812 A1      May 29, 2014

Related U.S. Application Data

(60) Provisional application No. 61/386,155, filed on Sep. 24, 2010.

(51) Int. Cl.
*A61C 8/00* (2006.01)
(52) U.S. Cl.
CPC ............. *A61C 8/0056* (2013.01); *A61C 8/0001* (2013.01); *A61C 8/005* (2013.01); *A61C 8/0022* (2013.01); *A61C 8/0068* (2013.01); *A61C 8/0069* (2013.01); *A61C 8/006* (2013.01)

(58) Field of Classification Search
CPC ...... A61C 8/005; A61C 8/0058; A61C 8/006; A61C 8/0068; A61C 8/0069; A61C 8/007
USPC ........................................ 433/172–176, 201.1
See application file for complete search history.

(56) References Cited

U.S. PATENT DOCUMENTS

| | | | | |
|---|---|---|---|---|
| 5,030,095 A | * | 7/1991 | Niznick | 433/173 |
| 5,069,622 A | * | 12/1991 | Rangert et al. | 433/173 |
| 5,135,395 A | * | 8/1992 | Marlin | 433/174 |

(Continued)

FOREIGN PATENT DOCUMENTS

| CN | 101489501 A | 7/2009 |
|---|---|---|
| CN | 103118625 A | 5/2013 |

(Continued)

OTHER PUBLICATIONS

"International Application Serial No. PCT/US2011/043784, International Preliminary Report on Patentability mailed Apr. 4, 2013", 7 pgs.

(Continued)

*Primary Examiner* — Cris L Rodriguez
*Assistant Examiner* — Hao D Mai
(74) *Attorney, Agent, or Firm* — Schwegman Lundberg & Woessner, P.A.

(57) ABSTRACT

A multi-unit dental implant system including a dental implant, a straight abutment, an angled abutment, and a plurality of copings or other components configured to universally fit on the cone-section of the straight abutment and the cone-section of the angled abutment.

14 Claims, 17 Drawing Sheets

(56) References Cited

U.S. PATENT DOCUMENTS

| | | | |
|---|---|---|---|
| 5,238,405 A * | 8/1993 | Marlin | 433/173 |
| 5,302,126 A * | 4/1994 | Wimmer et al. | 433/173 |
| 5,316,477 A * | 5/1994 | Calderon | 433/173 |
| 5,362,235 A * | 11/1994 | Daftary | 433/172 |
| 5,368,483 A * | 11/1994 | Sutter et al. | 433/173 |
| 5,577,912 A * | 11/1996 | Prins | 433/172 |
| 5,620,323 A * | 4/1997 | Bressman et al. | 433/174 |
| 5,662,474 A * | 9/1997 | Jorneus et al. | 433/172 |
| 5,667,384 A * | 9/1997 | Sutter et al. | 433/172 |
| 5,823,776 A * | 10/1998 | Duerr et al. | 433/173 |
| 5,947,733 A | 9/1999 | Sutter et al. | |
| 5,989,028 A * | 11/1999 | Niznick | 433/173 |
| 5,997,299 A * | 12/1999 | Unger | 433/173 |
| 6,227,856 B1 * | 5/2001 | Beaty et al. | 433/172 |
| 6,280,194 B1 * | 8/2001 | Bjorn et al. | 433/174 |
| 6,663,388 B1 * | 12/2003 | Schar et al. | 433/173 |
| 6,663,390 B2 * | 12/2003 | Riley et al. | 433/173 |
| 7,059,854 B2 * | 6/2006 | Wu | 433/173 |
| 7,112,063 B2 * | 9/2006 | Bulard et al. | 433/174 |
| 7,632,095 B2 * | 12/2009 | Ostman et al. | 433/173 |
| 7,866,981 B2 * | 1/2011 | Brajnovic | 433/173 |
| 7,905,727 B2 * | 3/2011 | Kikuchi | 433/189 |
| 8,142,193 B2 * | 3/2012 | Bar Shalom | 433/173 |
| 8,348,668 B2 * | 1/2013 | Lauridsen et al. | 433/173 |
| 2003/0013068 A1 * | 1/2003 | Gittleman | 433/173 |
| 2006/0183078 A1 | 8/2006 | Niznick | |
| 2006/0286509 A1 | 12/2006 | Bassett et al. | |
| 2009/0117520 A1 * | 5/2009 | Kikuchi | 433/174 |
| 2011/0097687 A1 * | 4/2011 | Engman | 433/174 |

FOREIGN PATENT DOCUMENTS

| | | |
|---|---|---|
| JP | 3012791 U | 6/1995 |
| JP | 2008546448 A | 12/2008 |
| JP | 2013540001 A | 10/2013 |
| WO | WO-2012039819 A1 | 3/2012 |

OTHER PUBLICATIONS

"International Application Serial No. PCT/US2011/043784, International Search Report mailed Nov. 9, 2011", 3 pgs.

"Chinese Application Serial No. 201180045682.2, Voluntary Amendment filed Sep. 13, 2013", (W/English Translation of Claims), 9 pgs.

"Chinese Application Serial No. 201180045682.2, Office Action mailed Dec. 1, 2014", (W/English Translation), 21 pgs.

"European Application Serial No. 11733983.8, Preliminary Amendment filed Nov. 18, 2013", 8 pgs.

"International Application Serial No. PCT/US2011/043784, Preliminary Amendment filed Jan. 5, 2012", 7 pgs.

"International Application Serial No. PCT/US2011/043784, Written Opinion mailed Nov. 9, 2011", 5 pgs.

"Japanese Application Serial No. 2013-530144, Office Action mailed Jun. 2, 2015", W/English Translation, 7 pgs.

\* cited by examiner

DENTAL IMPLANT AND ABUTMENT SYSTEM

RELATED APPLICATIONS

This patent application is a U.S. National Stage Filing under 35 U.S.C. §371 of International Patent Application Serial No. PCT/US2011/043784 filed on Jul. 13, 2011 and published on Mar. 29, 2012 as WO 2012/039819 A1, which claims the benefit of priority of U.S. Provisional Patent Application Ser. No. 61/386,155 filed on Sep. 24, 2010, the benefit of priority of each of which is claimed hereby and each of which is incorporated by reference herein in its entirety.

TECHNICAL FIELD

The disclosure is directed to abutments and other components for use with a dental implant. More particularly, the disclosure is directed to a selection of abutments for use with dental implants which provide versatility to a clinician while reducing the total number of components needed.

BACKGROUND

Dental implants are commonly used as anchoring members for dental restorations. The dental implant is typically threaded into a bore which is drilled into the patient's mandible or maxilla. The implant provides an anchoring member for a dental abutment, which in turn provides an interface between the implant and a dental restoration. It may be desirable to provide a multi-unit dental implant system which provides a clinician much versatility of component selection while reducing the total number of components required, therefore simplifying the entire system.

SUMMARY

The disclosure is directed to several alternative designs, materials and methods of manufacturing medical device structures and assemblies.

Accordingly, one illustrative embodiment is a multi-unit dental implant system. The system includes a dental implant including a threaded shaft having external threads and a central bore including an internal threaded portion. The system also includes a straight abutment and an angled abutment. The straight abutment includes an external threaded portion complementary to the internal threaded portion of the dental implant. The straight abutment includes a cone-section configured to receive a coping thereon. The angled abutment includes a body portion and a retaining screw insertable into a bore of the body portion. The body portion includes an anti-rotation feature configured to be inserted into the bore of the dental implant which prevents relative rotation between the angled abutment and the dental implant while the retaining screw secures the body portion to the dental implant with an external threaded portion complementary to the internal threaded portion of the dental implant. The body portion of the angled abutment includes a cone-section configured to receive a coping thereon. The system also includes a plurality of copings configured to universally fit on the cone-section of the straight abutment and the cone-section of the angled abutment.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
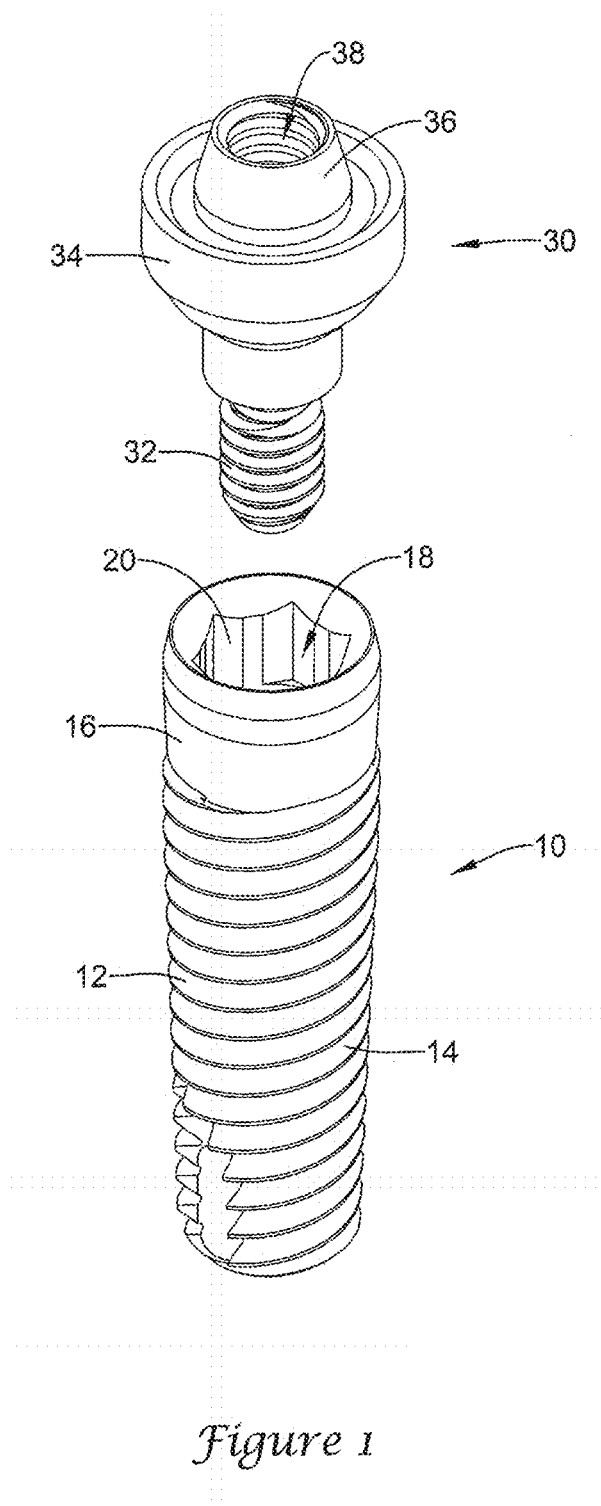
FIG. 1 is a perspective exploded view of a straight abutment and a dental implant.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 2:
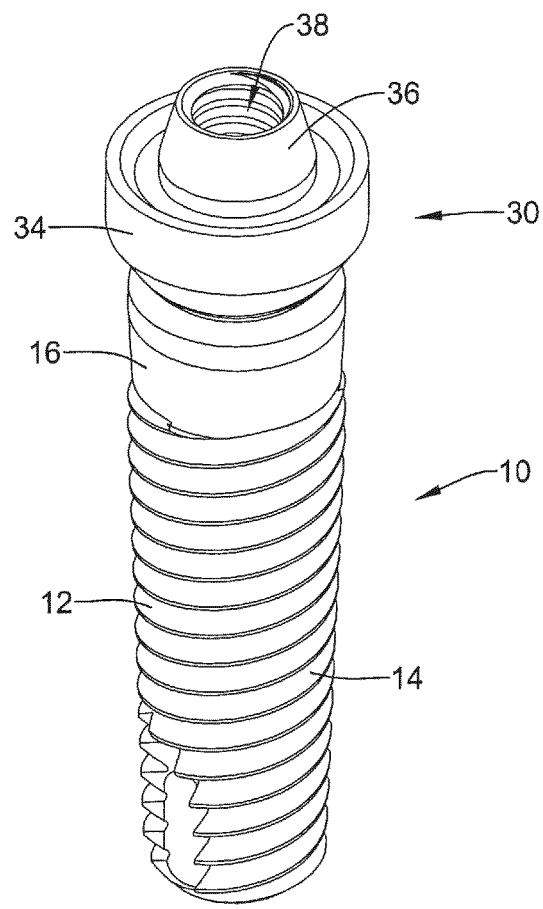
FIG. 2 is a perspective view of a straight abutment coupled to a dental implant.

FIGS. 1 and 2 illustrate a straight abutment 30 configured to be secured to a dental implant 10 for use in a dental restoration. The implant 10 may be generally cylindrical in shape, or tapered in shape, for example. The dental implant 10 may be a unitary member formed of a biocompatible material, such as titanium or stainless steel, for example. The implant 10 may include a head portion 16 at a coronal or proximal end of the implant 10 and a stem portion 12 extending from the head portion 16 to an apical or distal end of the implant 10. The stem portion 12 may include external threading 14 or other engagement features such as a porous metal scaffold for engagement with a bone during implantation of the dental implant 10.

The implant 10 may include a bore 18 extending into the implant from the coronal or proximal end of the implant 10. The central axis of the bore 18 may be co-axial with the central longitudinal axis of the implant 10. The proximal end of the bore 18 may be configured to receive a driver for rotationally inserting the implant 10 in a bone. For example, the proximal end of the bore 18 may include an internal hex 20 for receiving a hex driver therein. The implant 10 may also include an abutment interface structure for attaching an abutment to the implant 10. In some instances, the internal hex 20 may be provided as at least one component of the abutment interface structure. Although the abutment interface structure between the implant 10 and an abutment is shown as an internal hex 20 within the implant 10 which receives an external hex of an abutment as described below, in some instances the arrangement may be reversed. Also, other types of implant/abutment interfaces are contemplated, such as splines, octagons, lobes, torx, other geometric shapes, and other engaging configurations.

Figure 2A:
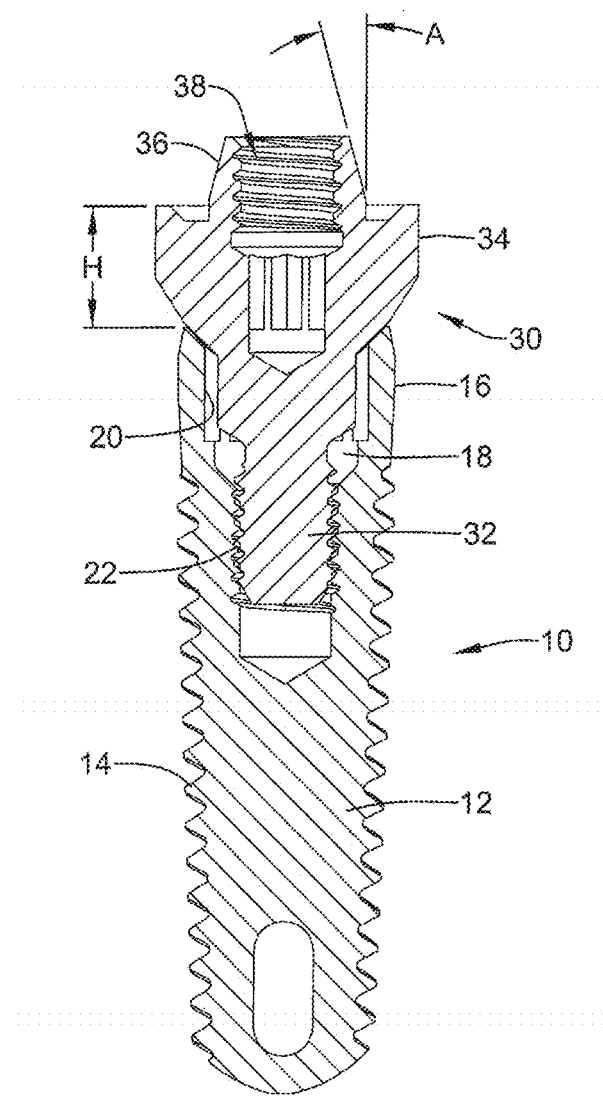
FIG. 2A is a cross-sectional view of the straight abutment coupled to the dental implant of FIG. 2.
Figure 4:
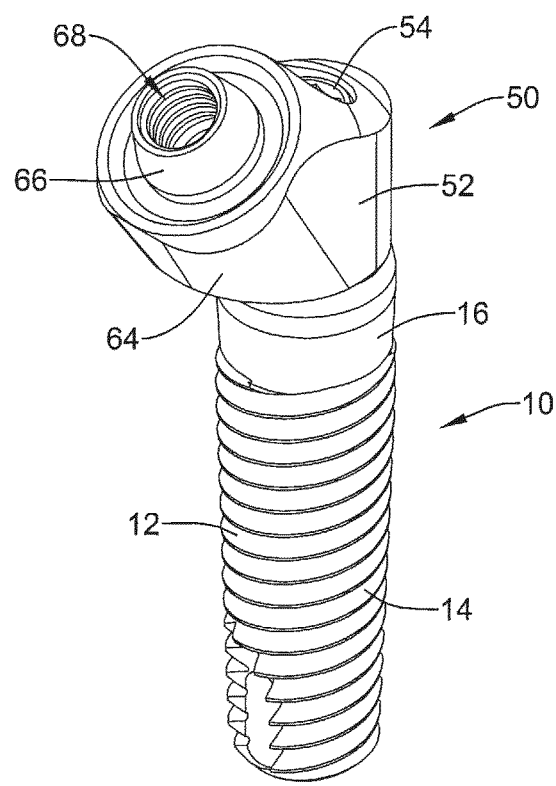
FIG. 4 is a perspective view of an angled abutment coupled to a dental implant.
Figure 4A:
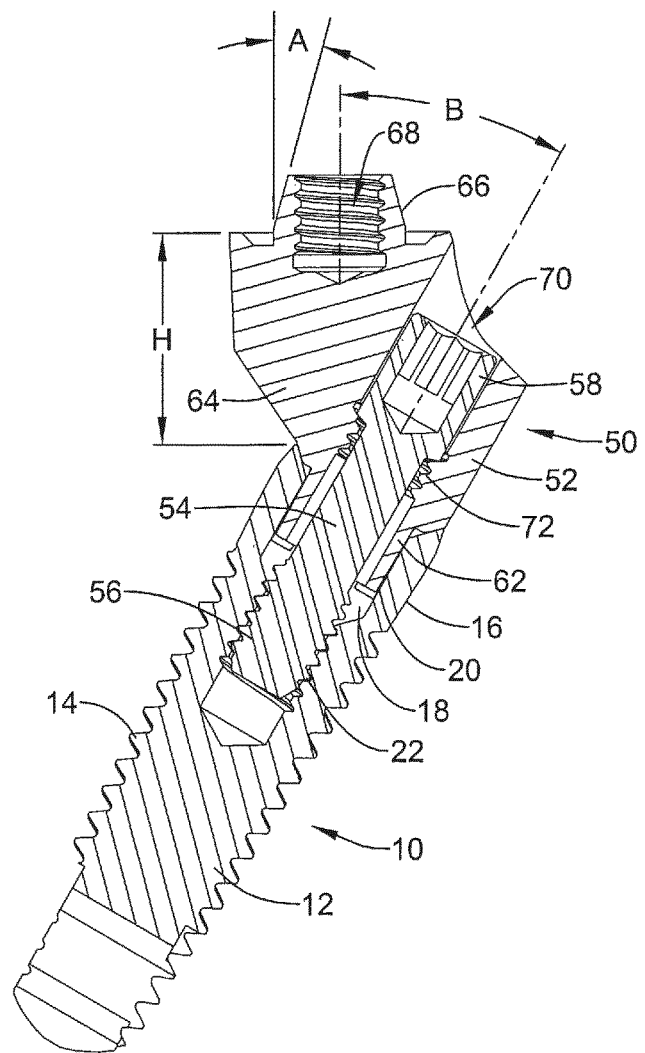
FIG. 4A is a cross-sectional view of the angled abutment coupled to the dental implant of FIG. 4.

The abutment interface structure may additionally or alternatively include an internally threaded portion 22 of the bore 18, as shown in FIGS. 2A and 4A for threadably engaging a component of an abutment to attach an abutment to the implant 10.

The straight abutment 30 may be configured to be secured to the implant 10. For example, the straight abutment 30 may include an externally threaded portion 32 configured to mate with and threadably engage the internally threaded portion 22 of the bore 18. The straight abutment 30, which may be a unitary member, may also include a cuff 34 and a cone portion 36 having a threaded bore 38 extending therein. The straight abutment 30 may be configured such that the central longitudinal axis of the straight abutment 30, which is the central longitudinal axis of the externally threaded portion 32 and the threaded bore 38, is co-axial with the central longitudinal axis of the implant 10.

As shown in FIG. 2A, the tapered cone portion 36 may have an angle A in the range of about 3.5° to about 20°, and the described system may include a series of straight abutments 30 having different cone angles A between about 3.5° to about 20° in ascending increments. Also shown in FIG. 2A, the cuff 34 may have a height H in the range of about 0 mm to about 7 mm, and the described system may include a series of straight abutments 30 having different cuff 34 heights H between about 0 mm to about 7 mm, for example in 1 mm increments.

Figure 3:
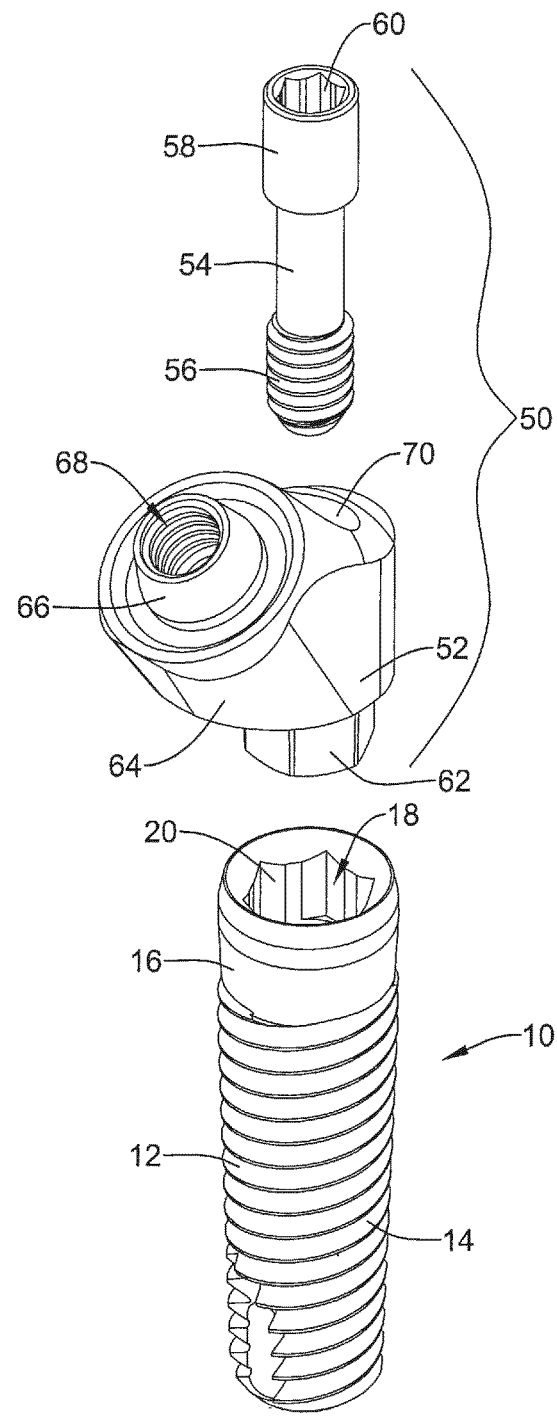
FIG. 3 is a perspective exploded view of an angled abutment and a dental implant.

FIGS. 3 and 4 illustrate an angled abutment 50 configured to be secured to the dental implant 10 for use in a dental restoration. The angled abutment 50 may be configured to be secured to the implant 10, thus not require different implants 10 to be used depending on the chosen abutment.

The angled abutment 50 may include a body portion 52 and a retaining screw 54 configured to secure the body portion 52 to the implant 10. The body portion 52 of the angled abutment 50 may include an anti-rotation interface structure 62 configured to mate with and complement the abutment interface structure 20 of the implant 10 to prevent rotation of the angled abutment 50 relative to the implant 10 and allow for consistent rotational placement of the angled abutment 50 at one of a plurality of predetermined rotational orientations about the central longitudinal axis of the implant 10. For example, the anti-rotation interface structure 62 may be a hex projection which is insertable into the internal hex 20 of the implant 10 at one of six angular orientations about the central longitudinal axis of the implant 10. It is noted that the anti-rotation interface structure 62 may be of a different configuration which mates with and complements the abutment interface structure of the implant 10 to prevent relative rotation between the angled abutment 50 and the implant 10.

The body portion 52 may be secured to the implant 10 with the retaining screw 54. For example, the retaining screw 54 may be positioned in the bore 70 and subsequent rotation of the retaining screw 54 using a driver engaged with the internal hex 60 of the head portion 58 may rotatably engage the externally threaded portion 56 of the retaining screw 54 with the internally threaded portion 22 of the bore 18 of the implant 10.

The bore 70 through the body portion 52 may include a threaded portion 72 located intermediate a proximal unthreaded portion and a distal unthreaded portion. The threaded portion 72 of the bore 70 may be sized such that the externally threaded portion 56 of the retaining screw 54 cannot pass through the threaded portion 72 without rotationally threading the retaining screw 54 through the threaded portion 52. The head portion 58 of the retaining screw 54 may be sized larger than the threaded portion 72 such that the head portion 58 cannot pass through the threaded portion 72.

As can be seen from FIG. 4A, the major diameter of the externally threaded portion 56 of the retaining screw 54 may be less than the diameter of the unthreaded proximal and distal portions of the bore 70, whereas the major diameter of the externally threaded portion 56 of the retaining screw 54 is less than the major diameter of the internally threaded portion 72 of the bore 70. Likewise, the minor diameter of the externally threaded portion 56 of the retaining screw 54 may be less than the minor diameter of the internally threaded portion 72 of the bore 70. Such a configuration permits the threaded portion 56 of the retaining screw 54 to be threaded through the threaded portion 72 of the bore 70, but prevents the threaded portion 56 to be axially passed through the threaded portion 72 without rotational movement.

The body portion 52, which may be a unitary member, may also include a cuff 64 and a cone portion 66 having a threaded bore 68 extending therein. The body portion 52 may also include a longitudinal bore 70 for receiving the retaining screw 54 therein for securing the body portion 52 to the implant 10. The angled abutment 50 may be configured such that the central longitudinal axis of the bore 70 of the angled abutment 50, which is the central longitudinal axis of the anti-rotation interface structure 62, is co-axial with the central longitudinal axis of the implant 10, while the central longitudinal axis of the cone portion 66 and threaded bore 68 is at an acute angle B to the central longitudinal axis of the bore 70.

As shown in FIG. 4A, the tapered cone portion 66 may have an angle A in the range of about 3.5° to about 20°, and the described system may include a series of angled abutments 50 having different cone angles A between about 3.5° to about 20° in ascending increments. Also shown in FIG. 4A, the cuff 64 may have a height H in the range of about 0 mm to about 7 mm, and the described system may include a series of angled abutments 50 having different cuff 64 heights H between about 0 mm to about 7 mm, for example in 1 mm increments. Furthermore, the angled abutment 50 may have an angle B between the central axis of the threaded bore 68 of the cone portion 66 and the central axis of the bore 70 and retaining screw 54 greater than 0° to about 30°, and the described system may include a series of angled abutments 50 having different angles B between about 10° to about 30°. For example, the system may include a series of angled abutments 50 having angles B of 10°, 15°, 17°, 20°, 25° and 30° options.

Figure 5:
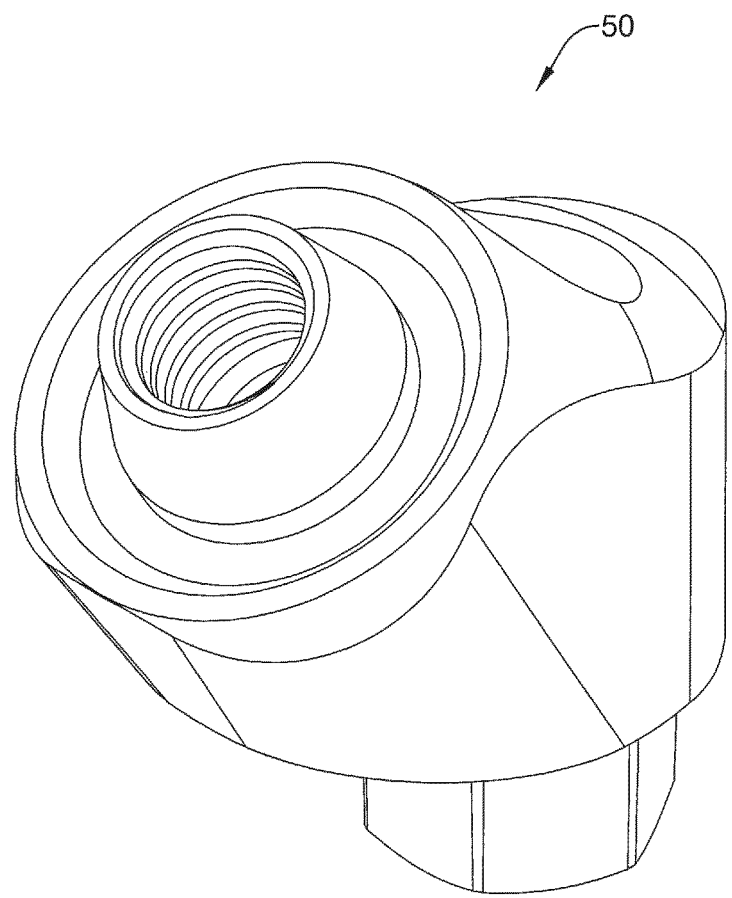
FIG. 5 is a first perspective view of an angled abutment for use with a dental implant.
Figure 6:
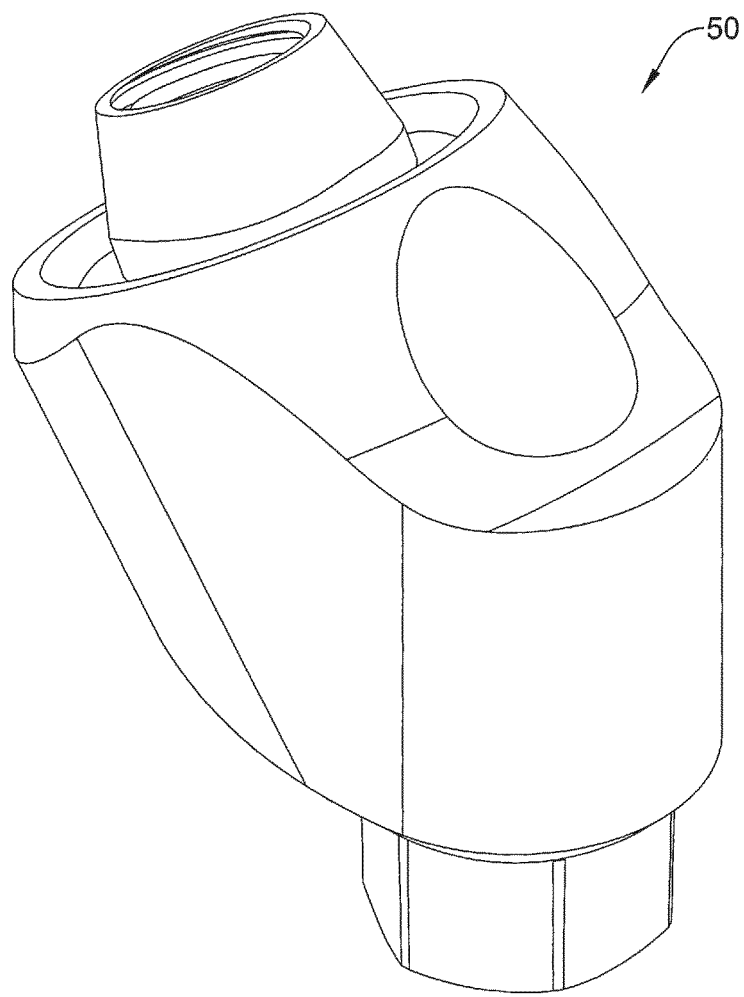
FIG. 6 is a second perspective view of the angled abutment for use with a dental implant.
Figure 7:
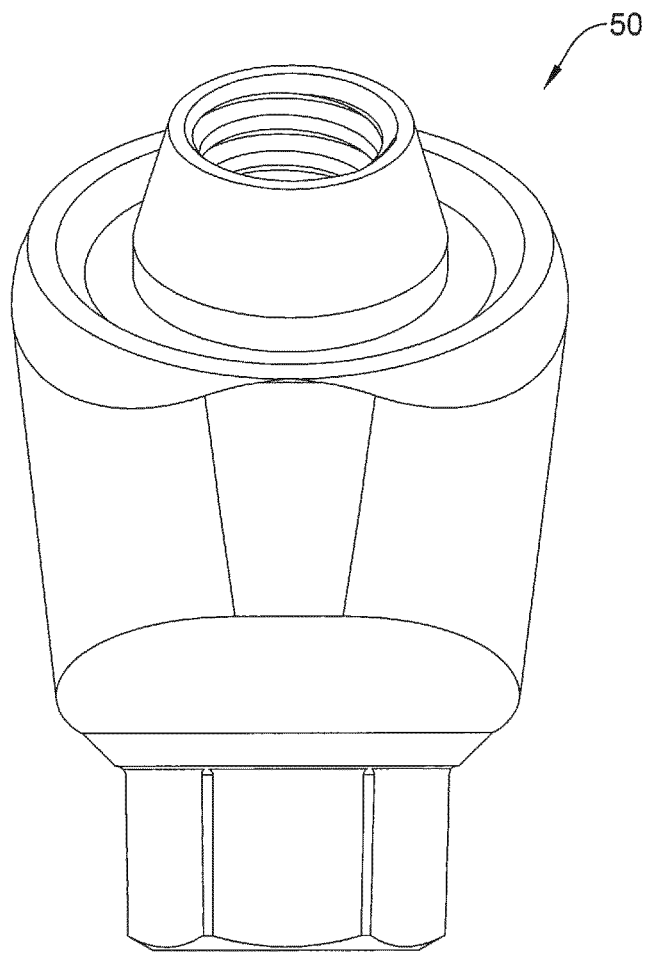
FIG. 7 is a front view of the angled abutment for use with a dental implant.
Figure 8:
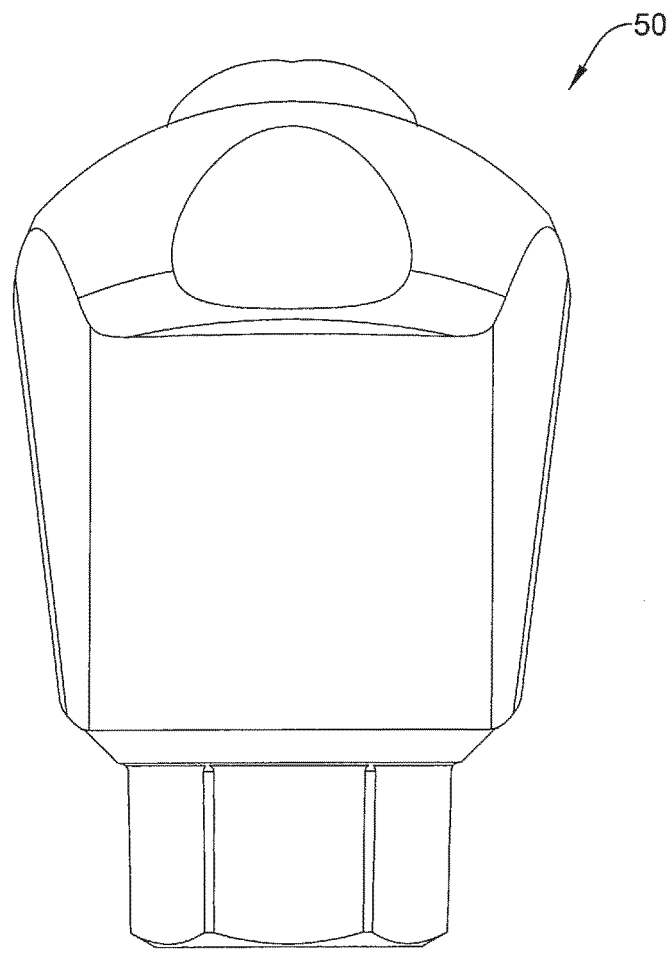
FIG. 8 is a back view of the angled abutment for use with a dental implant.
Figure 9:
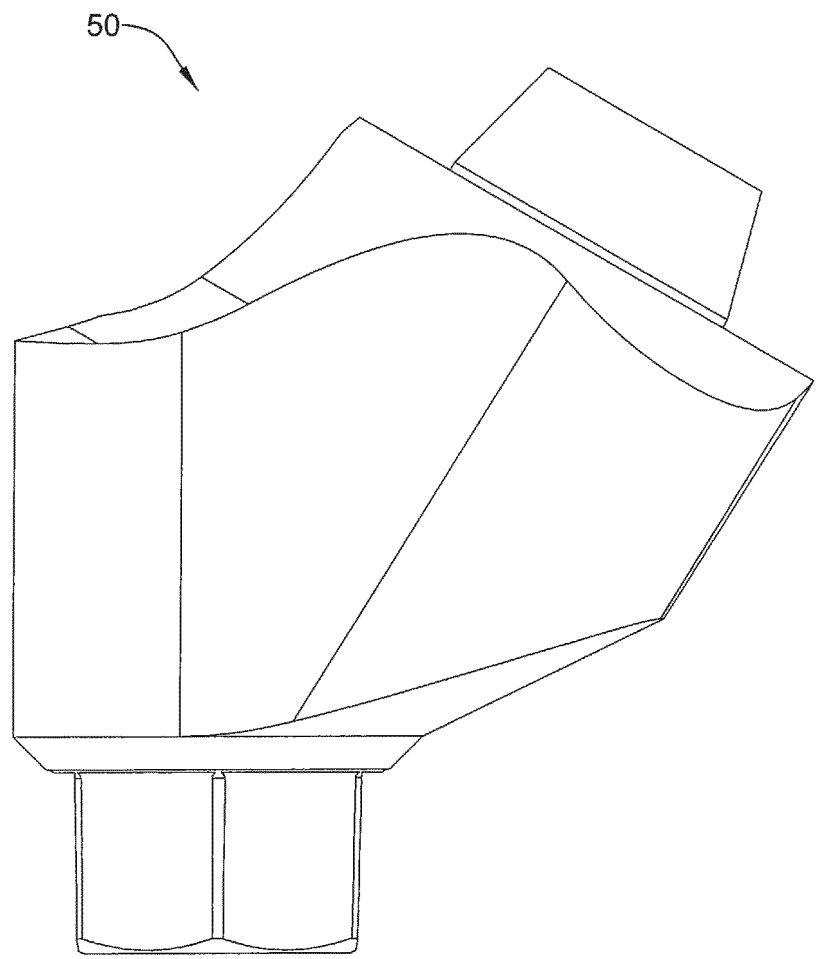
FIG. 9 is a first side view of the angled abutment for use with a dental implant.
Figure 10:
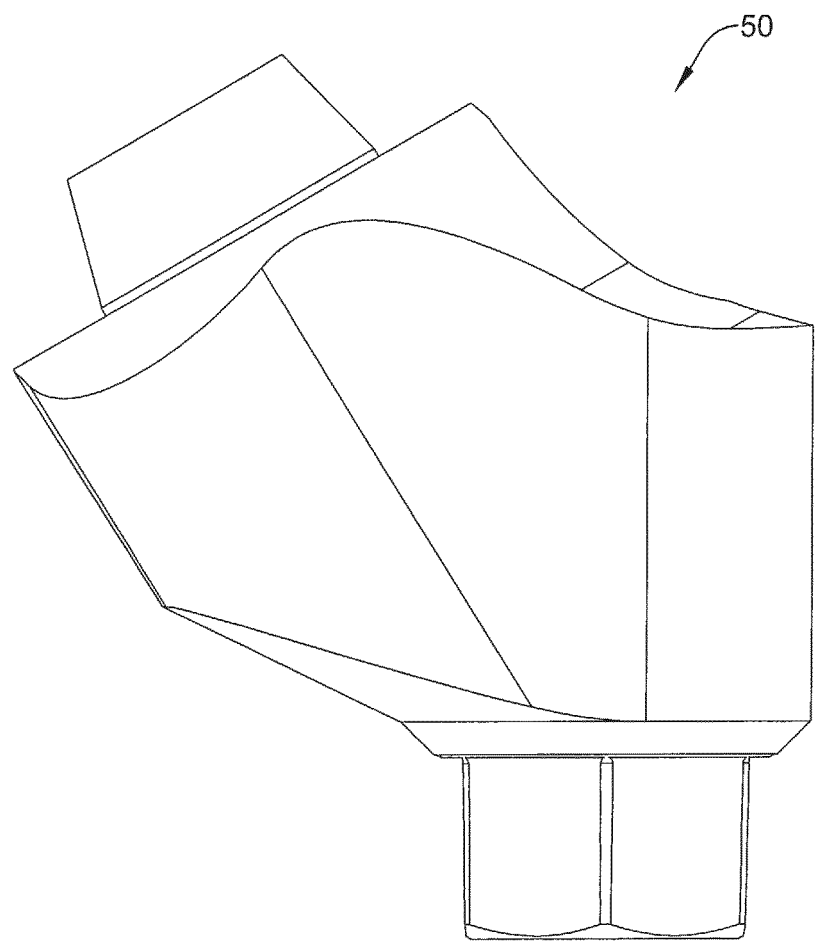
FIG. 10 is a second side view of the angled abutment for use with a dental implant, which is a mirror image of the first side view.
Figure 11:
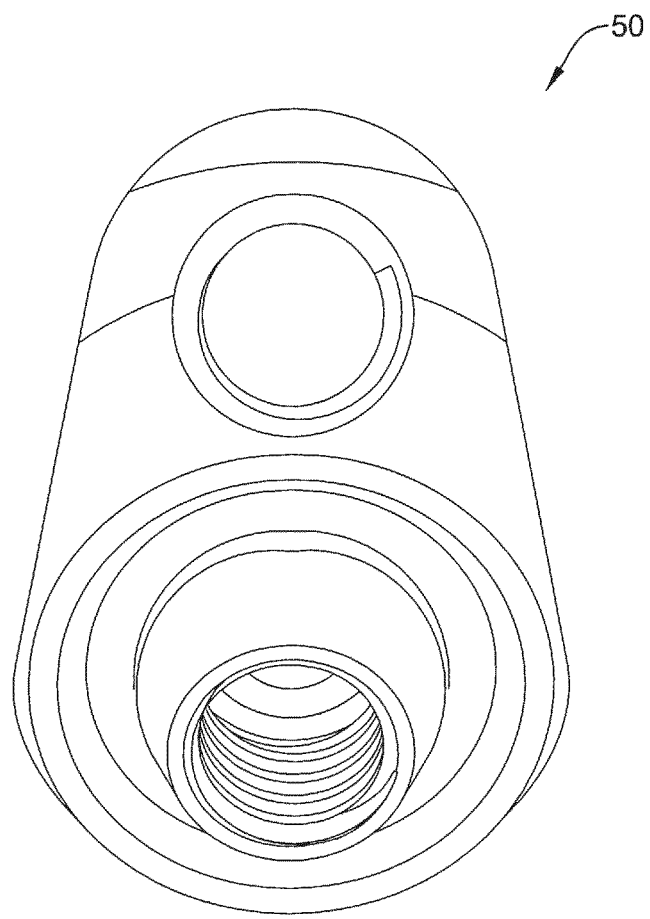
FIG. 11 is a top view of the angled abutment for use with a dental implant.
Figure 12:
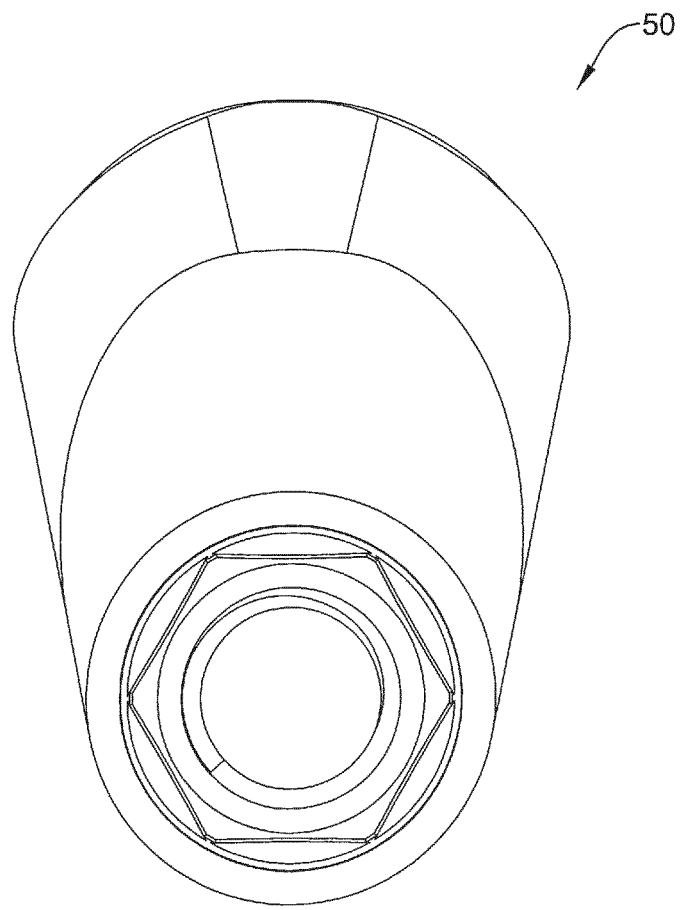
FIG. 12 is a bottom view of the angled abutment for use with a dental implant.

FIGS. 5-12 illustrate various views of the angled abutment 50, in which, FIG. 5 is a first perspective view, FIG. 6 is a second perspective view, FIG. 7 is a front view, FIG. 8 is a back view, FIG. 9 is a first side view, FIG. 10 is a second side view which is a mirror image of the first side view, FIG. 11 is a top view, and FIG. 12 is a bottom view of the angled abutment 50.

The cone portion 36 of the straight abutment 30 may be the same size and shape as the cone portion 66 of the angled abutment 50, and the internal threaded bore 38 of the straight abutment 30 may have the same threading size and pitch as the internal threaded bore 68 of the angled abutment 50, thus allowing a common coping and fastener to be used with both the straight abutment 30 and the angled abutment 50. As such, the system would require fewer components and provide increased compatibility between components of the system and universal usage of components of the system.

Figure 13:
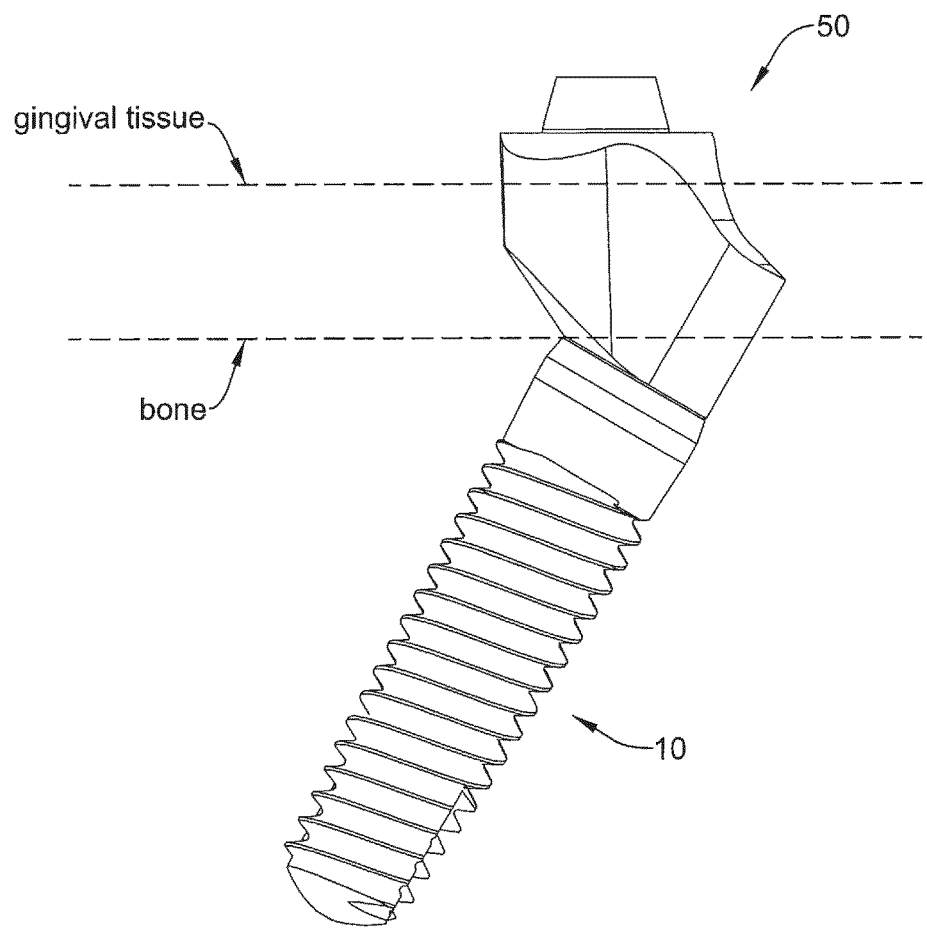
FIG. 13 illustrates an exemplary placement of the angled abutment and dental implant in the anatomy.
Figure 14:
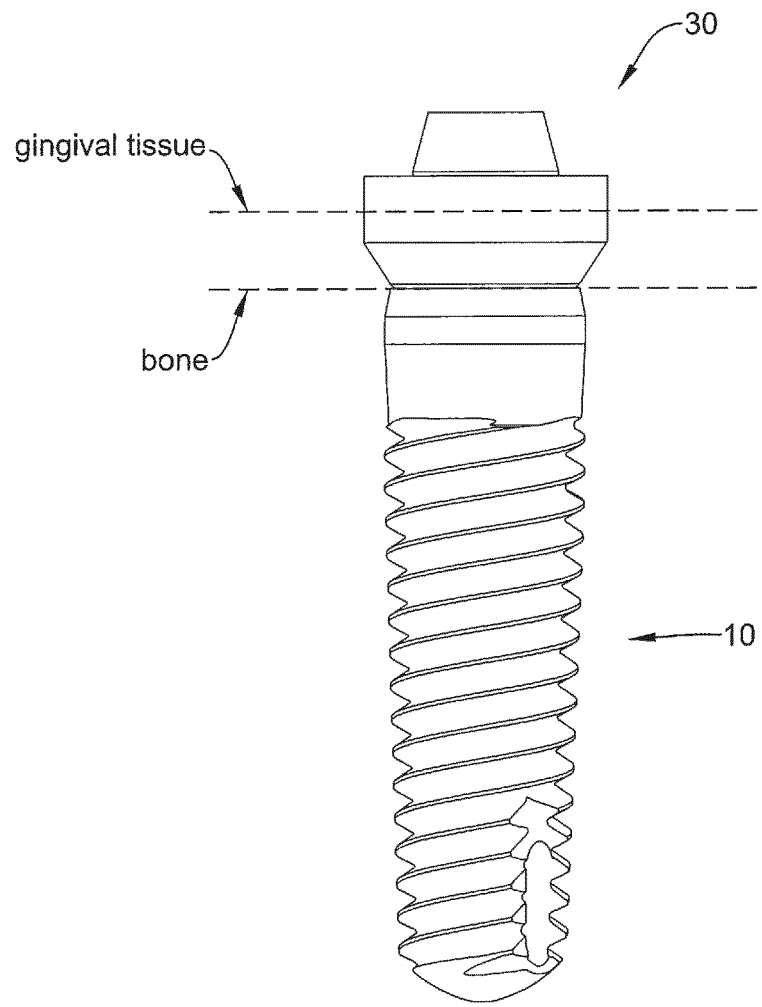
FIG. 14 illustrates an exemplary placement of the straight abutment and dental implant in the anatomy.

FIG. 13 illustrates a typical surgical placement of an implant 10 and angled abutment 50 in which the posterior implants 10 are placed at an angle to avoid anatomical features, and the angled abutment 50 is used to correct the angulation of the implant 10 to provide a common line of insertion and removal of the dental restoration. FIG. 14 illustrates a typical surgical placement of an implant 10 and straight abutment 30 which provides a common line of insertion and removal of the dental restoration. Thus, any combination of straight abutments 30 and angled abutments 50 may be used while maintaining a common line of insertion and removal of the dental restoration.

Figure 15:
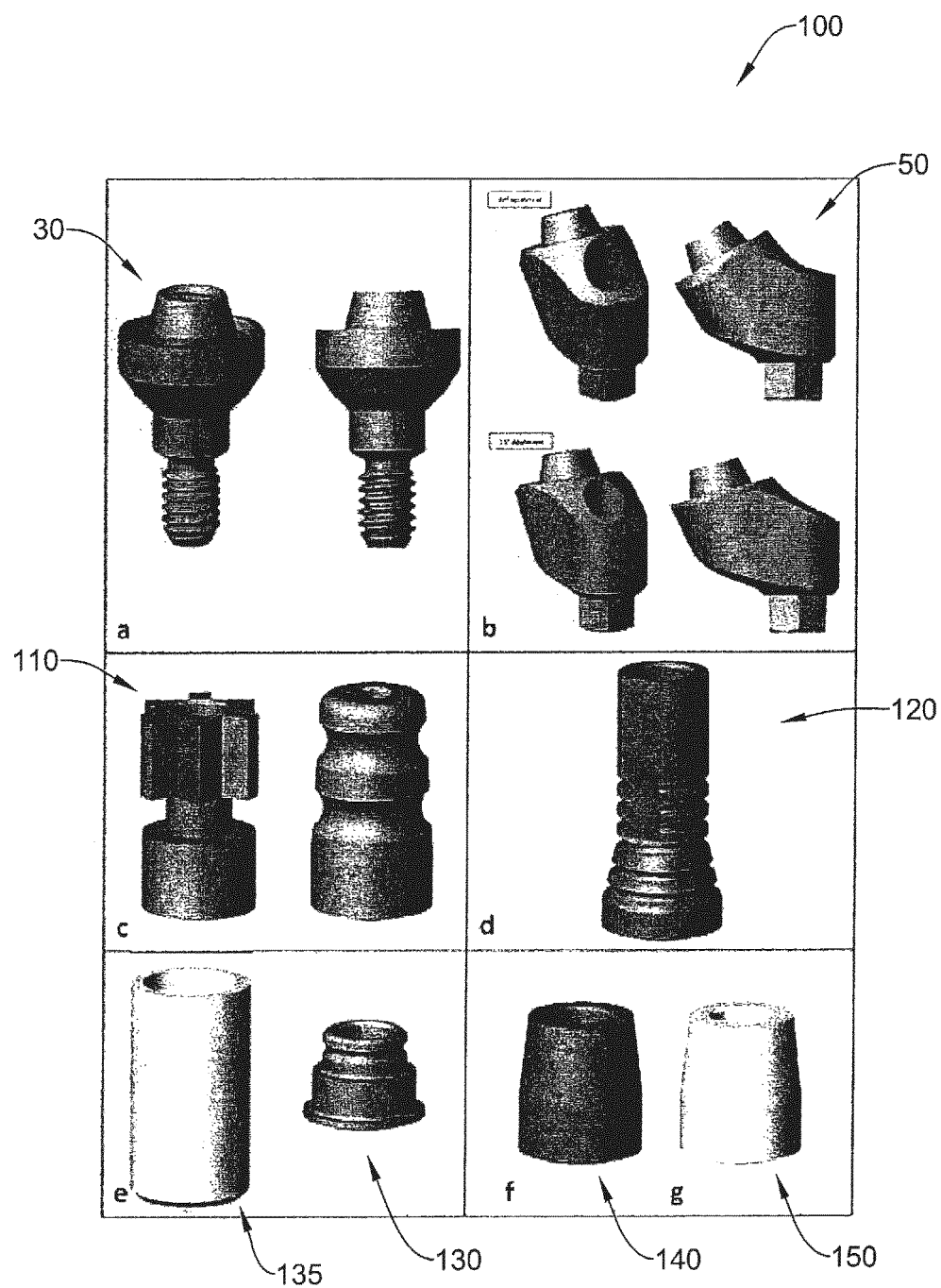
FIG. 15 illustrates additional components which may be universally used with either the straight abutments or angled abutments described herein.

Screw-retained abutment systems are commonly used in dental implantology to fabricate short span and full arch fixed removable dentures. The multi-unit dental implant system 100 described herein, components of which are shown at FIG. 15, simplifies the creation of a screw-retained restoration by providing a full selection of components to address differences in anatomy and different treatment options. In addition to dental implants 10, the multi-unit system 100 includes a series of straight abutments 30 of multiple cuff heights, and a series of angled abutments 50 of multiple cuff heights and angulations. The multi-unit system 100 also includes a universal transfer system 110 for performing abutment-level impressions. The universal transfer system 100 uses the same components for both angled and straight versions of the abutments 30, 50. Similarly, the multi-unit system 100 includes a universal coping system for both provisional and final restoration that is compatible with all cuff heights and angulations of the screw-retained abutments. The system includes temporary copings 120 (titanium or plastic), gold copings 130 with a plastic sheath 135 (final), titanium copings 140 (final), and plastic copings 150 (final). The system may also include copings made of ceramic or other materials such as acrylic or composite, if desired. The provided copings and transfers may be compatible for use with both the straight abutments 30 of the system 100 and the angled abutments 50 of the system 100. For instance, each of the copings may include a frustoconical or tapered cavity for receiving the cone portion 36, 66 of the abutment 30, 50 therein, such that the copings closely mate with the cone portion 36, 66. Thus, the copings may be interchangeably be used with the straight abutments 30 and the angled abutments 50.

In usage, the clinician would case plan and then place the dental implants, ideally to take advantage of location of the most bone and avoid anatomical structures. The clinician would then choose abutments to correct angulation and secure these abutments to the associated implant. The universal transfer would be used to record the position of the implant using standard impression taking techniques and the impression in turn would be used to create a stone model. The stone model would be used in the dental laboratory to create the final prosthetic restoration.

To facilitate creation of the final prosthetic restoration, the clinician may use the gold coping with plastic sheath to create a precious metal restoration. For example, a lost-wax investment-casting process may be used to cast the gold coping into the final prosthetic restoration. The coping may provide a precise match to the cone feature of the abutment. Alternatively, the all-plastic coping may be used in the casting. Another process for creating a dental restoration may use the titanium coping.

The design and part offering of the multi-unit system as described herein, may provide a clinician much versatility while reducing the total number of components required, therefore simplifying the entire system. Design features are also aimed to increase the simplicity of the system. For example, the unitary abutment construction of the straight abutments and/or the anti-rotational interface formed in the unitary body portion of the angle abutment in conjunction with the separate retaining screw contribute to the simplicity of the system, as well as the universal nature of the transfers and copings. Thus, the multi-unit dental implant system offers the user an advantage because the system is versatile due in part to the multiple cuff height and angulation options, as well as to the availability of a full complement of copings for creation of a tooth prosthetic. The system also benefits from the commonality of parts between different cuff height and angulation options and the resulting reduction in parts count.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A multi-unit dental implant system, comprising:
a dental implant including a threaded shaft having external threads and a central bore including an internal threaded portion, the central bore defining a central longitudinal axis;
an angled abutment including a body portion and a retaining screw insertable into a bore of the body portion, the body portion including an anti-rotation portion configured to be inserted into the central bore of the dental implant to prevent relative rotation between the angled abutment and the dental implant, the retaining screw is configured to secure the body portion to the dental implant with an external threaded portion complementary to the internal threaded portion of the dental implant, the body portion of the angled abutment including a tapered cone portion configured to receive a coping thereon;
a straight abutment, configured to be interchangeable with the angled abutment, including an external threaded portion complementary to the internal threaded portion of the dental implant, the straight abutment including a cone portion configured to receive a coping thereon; and
a plurality of copings, each of the copings having a tapered cavity configured to universally mate, interchangeably, on the cone portion of the straight abutment and the tapered cone portion of the angled abutment;
wherein the bore of the body portion includes a first axis adapted to be coaxial with the central longitudinal axis of the dental implant, wherein the angled abutment includes a second bore within the tapered cone portion terminating prior to the bore of the body portion, the second bore defining a second axis oriented at an acute angle with respect to the first axis, and wherein the second bore is threaded.

2. The multi-unit dental implant system of claim 1, wherein the cone portion of the straight abutment includes a threaded bore.

3. The multi-unit dental implant system of claim 2, wherein the threaded bore of the cone portion of the straight abutment and the second bore of the angled abutment both include threading of a same pitch and diameter.

4. The multi-unit dental implant system of claim 1, wherein the plurality of copings include a tapered cavity configured to interchangeably engage with the cone portion of the straight abutment and the tapered cone portion of the angled abutment.

5. The multi-unit dental implant system of claim 1, wherein the bore of the body portion includes an internally threaded portion axially spaced from the internally threaded portion of the central bore, when the dental implant is constructed.

6. The multi-unit dental implant system of claim 5, wherein the two spaced apart threaded portions of the constructed dental implant have equally sized diameters and threads.

7. The multi-unit dental implant system of claim 1, wherein an outer surface of the tapered cone portion of the angled abutment is tapered at an angle of about 3.5° to about 20°.

8. The multi-unit dental implant system of claim 1, wherein the acute angle is less than about 30°.

9. The multi-unit dental implant system of claim 1, wherein the body portion comprises a cuff at its interface with the implant.

10. The multi-unit dental implant system of claim 9, wherein the cuff of the angled abutment underlies the tapered cone portion, and has a height of up to 7 mm.

11. A multi-unit dental implant system, comprising:
a dental implant including a threaded shaft having external threads and a central bore including an internal threaded portion, the central bore defining a central longitudinal axis;
an angled abutment including a body portion and a retaining screw insertable into a bore of the body portion, the body portion including an anti-rotation portion configured to be inserted into the central bore of the dental implant to prevent relative rotation between the angled abutment and the dental implant, the retaining screw including a head portion defining a hex structure configured to receive a driver so as to secure the body portion to the dental implant with an external threaded portion complementary to the internal threaded portion of the dental implant, the body portion of the angled abutment including a tapered cone portion configured to receive a coping thereon;
a straight abutment including an external threaded portion complementary to the internal threaded portion of the dental implant, the straight abutment including a cone portion configured to receive a coping thereon, wherein the angled abutment and the straight abutment are configured to be interchangeably coupled to the dental implant; and
a plurality of copings, each of the copings having a tapered cavity configured to universally mate, interchangeably, on the cone portion of the straight abutment and the tapered cone portion of the angled abutment;
wherein the bore of the body portion includes a first axis adapted to be coaxial with the central longitudinal axis of the dental implant, wherein the angled abutment includes a second bore within the tapered cone portion terminating prior to the bore of the body portion, the second bore defining a second axis oriented at an acute angle with respect to the first axis, and wherein the second bore is threaded.

12. The multi-unit dental implant system of claim 11, wherein the anti-rotation portion is configured to position the angled abutment within the central bore of the dental implant at a predetermined rotational orientation relative to the central longitudinal axis of the central bore.

13. The multi-unit dental implant system of claim 11, further comprising a plurality of angled abutments each including a unique angle defined by the second axis with respect to the first axis.

14. A deconstructed multi-unit dental implant system, comprising:
a dental implant including a threaded shaft having external threads and a central bore including an internal threaded portion, the central bore defining a central longitudinal axis;
an angled abutment including a body portion and a retaining screw insertable into a bore of the body portion, the body portion including an anti-rotation portion configured to be inserted into the central bore of the dental implant to prevent relative rotation between the angled abutment and the dental implant, the retaining screw is configured to secure the body portion to the dental implant with an external threaded portion complementary to the internal threaded portion of the dental implant, the body portion of the angled abutment including a tapered cone portion configured to receive a coping thereon;
a straight abutment, configured to be interchangeable with the angled abutment, including an external threaded portion complementary to the internal threaded portion of the dental implant, the straight abutment including a cone portion configured to receive a coping thereon; and a plurality of copings having a tapered cavity configured to interchangeably mate with the cone portion of the straight abutment and the tapered cone portion of the angled abutment;

wherein the bore of the body portion includes a first axis adapted to be coaxial with the central longitudinal axis of the dental implant, wherein the angled abutment includes a second bore within the tapered cone portion terminating prior to the bore of the body portion, the second bore defining a second axis oriented at an angle of about 10° to about 30° with respect to the first axis, and wherein the second bore is threaded.

* * * * *